United States Patent [19]

Weisburg

[11] Patent Number: 5,466,577
[45] Date of Patent: Nov. 14, 1995

[54] NUCLEIC ACID PROBES FOR THE DETECTION OF LYME DISEASE SPIROCHETES

[75] Inventor: William G. Weisburg, Milford, Mass.

[73] Assignee: Amoco Corporation

[21] Appl. No.: 144,212

[22] Filed: Oct. 27, 1993

Related U.S. Application Data

[63] Continuation of Ser. No. 773,351, Oct. 8, 1991, abandoned, which is a continuation of Ser. No. 416,072, Oct. 2, 1989, abandoned.

[51] Int. Cl.$^6$ .................................................... C12Q 1/68
[52] U.S. Cl. ...................... 435/6; 536/24.32; 536/24.33; 435/91.2
[58] Field of Search .................. 435/91.2, 6; 536/24.32, 536/24.33

[56] References Cited

U.S. PATENT DOCUMENTS 4,683,195   7/1989   Mullis et al. ............................... 435/91

OTHER PUBLICATIONS

LeFebvre et al., J. Clin. Microbiol. 27(4):636–9, Apr. 1989.
Matthews et al. Analytical Biochem. 169: 1–25, 1988 (Feb. 1988).
Goodman et al., "A Unique DNA Clone Specific for *Bonelia* . . . ", *Clinical Research*, vol. 37(2), p. 429A, (1989).
Schwane et al., "Efficacy of Nucleic Acid Hybridization . . . ", *Annals of the New York Academy of Sciences*, vol. 539, pp. 419–421 (1988).
Schwan et al., "Identification of *Borrelia burgdorferi* . . . " *Journal of Clinical Microbiology*, vol. 27, No. 8, pp. 1734–1738 (1989, Aug.).
Burgdorfer et al., Science 216:1317–1319, 1982.
Johnson et al., Int. J. Syst. Bacteriol. 34:496–497, 1984.
Kohne et al., Biophysical Journal 8:1104–1118, 1968.
Pace and Campbell, Journal of Bacteriology 107:543–547, 1971.
Sogin, Sogin and Woese, Journal of Molecular Evolution 1:173–184, 1972.
Fox, Pechman and Woese, International J. of Syst. Bacteriology 27:44–57, 1977.
Chemical Abstracts, vol. 107, No. 9, Aug. 31, 1987, p. 362, abstract No. 73936x, Columbus, Ohio, US; L. Hayes et al.: "A short peptide sequence is conserved between three tick–borne Borrelia," & Biochem. Soc. Trans. 1987, 15(4), 644 *Abstract*.
Chemical Abstracts, vol. 112, No. 9, Feb. 1990, p. 410, abstract No. 73093y, Columbus, Ohio, US; P. A. Rosa et al.: "A specific and sensitive assay for the Lyme disease spirochete Borrelia burgdorferi using the polymerase chain reaction," J. Infect. Dis. 1989, 160(6), 1018–29 *Abstract*.
Chemical Abstracts, vol. 110, No. 21, May 1989, p. 406, abstract No. 189215c, Columbus, Ohio, US; R. B. LeFebvre et al.: "Characterization of Borrelia burgdorferi isolates by restriction endonuclease analysis and DNA hybridization," & J. Clin. Microbiol. 1989, 27(4), 636–9 *Abstract*.
Chemical Abstracts, vol. 113, No. 5, Jul. 30, 1990, p. 294, abstract No. 37190q, Columbus, Ohio, US; D. C. Malloy et al.: "Detection of Borrelia burgdorferi using the polymerase chain reaction," & J. Clin. Microbiol. 1990, *Abstract*.
Biological Abstracts, vol. 88, No. 7, Apr. 1989, abstract No. 75033, Philadelphia, Pa., US; T. G. Schwan et al. "Identification probes," & J. Clin. Microbiol. 27(8): 1734–1738. 1989 *Abstract*.
J. Clin. Chem. Biochem., vol. 25, No. 9, 1987, p. 573; U. B. Gobel et al.: "Synthetic oligodeoxynucleotides complementary to ribosomal RNA as probes for rapid detection & identification of fastidious pathogenic bacteria" *Whole article*.

*Primary Examiner*—Magaret Parr
*Assistant Examiner*—Scott William Houtteman
*Attorney, Agent, or Firm*—Norval B. Galloway

[57] ABSTRACT

Nucleic acid probes are described for detecting bacteria capable of causing Lyme disease. These probes complement the ribosomal ribonucleic acid sequences unique to Borrelia spirochetes, and as such can detect the rRNA, rDNA, or polymerase chain reaction amplification products of these genes. These probes, plus the described amplification primers, can be used to detect the etiological agent of Lyme disease in human or veterinary samples, and for determining the infective potential of Ixodes ticks.

16 Claims, 1 Drawing Sheet

NUCLEIC ACID PROBES FOR THE DETECTION OF LYME DISEASE SPIROCHETES

CROSS-REFERENCE TO RELATED APPLICATION

This is a continuation of application Ser. No. 773,351, filed Oct. 8, 1991, now abandoned, which is a continuation of application Ser. No. 416,072, filed Oct. 2, 1989, now abandoned.

FIELD OF THE INVENTION

This invention relates to detection of bacteria belonging to the species *Borrelia burgdorferi* and related species of tick-borne spirochetes capable of causing human and veterinary disease. More specifically, it provides nucleic acid probes and compositions along with methods for their use for the specific detection of Lyme disease causing bacteria.

BACKGROUND OF THE INVENTION

Lyme borreliosis, Lyme disease, Lyme arthritis, Bannwarth's syndrome, or erythema chronicum migrans (ECM) are synonymous designations for a zoonotic spirochetal infection transmitted by the bite of ticks of the genus Ixodes. Although the disease was known in Europe for quite some time, it was not discovered in the United States until a 1975 arthritis epidemic occurred in Connecticut. A presumptive etiological agent was isolated from a tick in 1982 (Burgdorfer et. al, *Science* 216:1317–1319, 1982). In 1984, the spirochete was shown to be a member of the genus Borrelia, and formally named *Borrelia burgdorferi* (Johnson et. al, *Int. J. Syst. Bacteriol.* 34:496–497, 1984). As such, it is an evolutionary relative of *Borrelia hermsii, Borrelia turicatae, Borrelia anserina*, and other members of this arthropod associated genus of spiral bacteria.

Lyme disease is a serious chronic borrelial infection characterized by a diversity of symptoms at various stages. Approximately 3 to 14 days following the initiating tick bite, symptoms may include fever, flu-like illness, and the appearance of the ECM skin rash. Stage two, occurring weeks to months after the initial bite includes further skin involvement, arthritis, nervous system complaints, and cardiac pathology. Stage three is characterized by more severe arthritis and nervous system complications.

Diagnosis of Lyme disease is generally either differential or dependent on host antibody response. Isolation and culture of these bacteria as a diagnostic method is not considered technically or economically feasible. Differential diagnosis relies on time of year (tick season), residence in an endemic area, recollection of tick-bite history, and ECM rash. This diagnostic scheme suffers, respectively, from the chronic nature of the disease, infection of travellers, the incredibly small size of the ticks, and that not all patients experience the ECM rash. Diagnosis based on antibody response requires the seroconversion of infected individuals toward production of anti-*B. burgdorferi* antibodies. While the antibody approach works for many diagnostic problems, it fails for Lyme diagnosis for the following reasons:

The combination of low numbers of spirochetes and antigenically bland outermembrane yields weak host immune response.

Seroconversion takes some period of time after infection. During the height of spirochetemia, within weeks of the initial tick bite, a patient presenting with fever and ECM may fail to evince antibody.

The antibody response is transitory. During Stage two or Stage three, when circulating bacteria are fewest, antibody titers may be very low.

Cell mediated immunity may detract from circulating antibody signal, that is, classical host IgG and IgM response is decreased or absent due to masked antigens.

Most of the antibody tests rely on whole *Borrelia burgdorferi* preparations as target antigens, The major problem with this approach is cross-reactivity with an immunological response to other bacterial challenges. Most noteworthy is cross-reaction with anti-*Treponema pallidum* (syphilis) antibodies.

It is an aspect of the present invention to provide non-immunologically based assays thereby avoiding associated problems and to provide nucleic acid probes which are specific for tick-borne spirochetes capable of causing Lyme disease and related morbidity.

It is another aspect of the present invention to provide probes and assays particularly specific for the type strain of the species, *Borrelia burgdorferi* B31, American Type Culture Collection strain number 35210.

It is yet another aspect of the present invention to provide nucleic acid probes which can hybridize to target regions which can be rendered accessible to probes under normal assay conditions.

While Kohne et al. (*Biophysical Journal* 8:1104–1118, 1968) discuss one method for preparing probes to rRNA sequences, they do not provide the teaching necessary to make *Borrelia burgdorferi* specific probes or, in fact, any other probes to detect spirochete bacteria.

Pace and Campbell (*Journal of Bacteriology* 107:543–547, 1971) discuss the homology of ribosomal ribonucleic acids from diverse bacterial species and a hybridization method for quantitating such homology levels, Similarly, Sogin, Sogin and Woese (*Journal of Molecular Evolution* 1:173–184, 1972) discuss the theoretical and practical aspects of using primary structural characterization of different ribosomal RNA molecules for evaluating phylogenetic relationships. Fox, Pechman and Woese (*International Journal of Systematic Bacteriology* 27:44–57, 1977) discuss the comparative cataloging of 16S ribosomal RNAs as an approach to prokaryotic systematics. These references, however, fail to relieve the deficiency of Kohne's teaching with respect to Lyme spirochetes and in particular, do not provide Lyme spirochete specific probes useful in assays for detecting Lyme disease or its etiological agent, *Borrelia burgdorferi* and relatives. Ribosomes are of profound importance to all organisms because they serve as the only known means of translating genetic information into cellular proteins, the main structural and catalytic elements of life. A clear manifestation of this importance is the observation that all cells have ribosomes.

Ribosomes contain three distinct RNA molecules which, at least in *Escherichia coli*, are referred to as 5S, 16S and 23S rRNAs. These names historically are related to the size of the RNA molecules, as determined by their sedimentation rate. In actuality, however, ribosomal RNA molecules vary substantially in size between organisms. Nonetheless, 5S, 16S, and 23S rRNA are commonly used as generic names for the homologous RNA molecules in any bacteria, and this convention will be continued herein. An additional convention used herein designates sequence position numbers analogous to those of the *Escherichia coli* 16S rRNA sequence (Brosius et al., PNAS (USA) 75:4801–4805, 1978).

As used herein, probe(s) refer to synthetic or biologically produced nucleic acids (DNA or RNA) which, by design or selection, contain specific nucleotide sequences that alloy them to hybridize under defined predetermined stringencies, specifically (i.e., preferentially, see next paragraph) to target nucleic acid sequences. In addition to their hybridization properties, probes also may contain certain constituents that pertain to their proper or optimal functioning under particular assay conditions. For example, probes may be modified to improve their resistance to nuclease degradation (e.g. by end capping), to carry detection ligands (e.g. fluorescien, 32-P, biotin, etc.), or to facilitate their capture onto a solid support (e.g., poly-deoxyadenosine "tails"—see FIG. 1). Such modifications are elaborations on the basic probe function which is its ability to usefully discriminate between target and non-target organisms in a hybridization assay.

Hybridization traditionally is understood as the process by which, under predetermined reaction conditions, two partially or completely complementary strands of nucleic acid are allowed to come together in an antiparallel fashion (one oriented 5' to 3', the other 3' to 5') to form a double-stranded nucleic acid with specific and stable hydrogen bonds, following explicit rules pertaining to which nucleic acid bases may pair with one another. The high specificity of probes relies on the low statistical probability of unique sequences occurring at random as dictated by the multiplicative product of their individual probabilities. These concepts are yell understood by those skilled in the art.

The stringency of a particular set of hybridization conditions is defined by the base composition of the probe/target duplex, as well as by the level and geometry of mispairing between the two nucleic acids.

Stringency may also be governed by such reaction parameters as the concentration and type of ionic species present in the hybridization solution, the types and concentrations of denaturing agents present, and/or the temperature of hybridization. Generally, as hybridization conditions become more stringent, longer probes are preferred if stable hybrids are to be formed. As a corollary, the stringency of the conditions under which a hybridization is to take place (e.g., based on the type of assay to be performed) will dictate certain characteristics of the preferred probes to be employed. Such relationships are well understood and can be readily manipulated by those skilled in the art.

As a general matter, dependent upon probe length, such persons understand stringent conditions to mean approximately 35° C.–65° C. in a salt solution of approximately 0.9 molar.

SUMMARY OF THE INVENTION

In accordance with the various principles and aspects of the present invention, there are provided nucleic acid probes and probe sets comprising deoxyribonucleic acid (DNA) or ribonucleic acid (RNA) sequences which hybridize, under specific conditions, to the ribosomal RNA molecules (rRNA) or rRNA genes (rDNA) of Borrelia spirochetes but which do not hybridize, under the same conditions, to the rRNA or rDNA of other bacteria which may be present in test samples. Therefore the probes of the present invention provide the basis for development of a valuable nucleic acid hybridization assay for the specific detection of Lyme disease, or its etiological agent, in clinical samples of blood, urine, cerebrospinal fluid, skin biopsy, saliva, synovial fluid, or other tissue or fluid samples from human patients or veterinary subjects. The probes also provide the basis for testing the tick vectors of Lyme disease—the genus Ixodes—to assess infectivity rates or endemic range.

In our experience nucleic acid hybridization based assays have been discovered to impart enhanced performance capabilities with respect to most currently available, microbiological or immunological methods for detection of bacteria in test samples, generally including:

a) increased sensitivity; i.e., the ability to detect said bacteria in a given sample more frequently;

b) potentially significant reductions in assay cost due to the use of inexpensive reagents and reduced labor;

c) accurate identification of even biochemically unusual strains of the target bacteria, or bacteria with dramatically different outer membrane proteins;

d) direct assay for the presence of the bacterium and consequent potential to quantify the etiological agents;

e) assay independent of the host's immune response schedule—much earlier detection is possible;

f) direct testing allows the monitoring of the efficacy of an antibiotic regime;

g) potential to detect said etiological agent in samples of tissue normally low in antibody titer such as skin.

It has been discovered that other advantages incurred by directing the probes of the present invention against rRNA include the fact that the rRNAs detected constitute a significant component of cellular mass. Although estimates of cellular ribosome content vary, actively growing *Borrelia burgdorferi* may contain upwards of 20,000 ribosomes per cell, and therefore 20,000 copies of each of the rRNAs (present in a 1:1:1 stiochiometry in ribosomes). In contrast, other potential cellular target molecules such as genes or RNA transcripts thereof, are less ideal since they are present in much lower abundance. A further unexpected advantage is that the rRNAs (and the genes specifying them) appear not to be subject to lateral transfer between contemporary organisms. Thus, the rRNA primary structure provides an organism-specific molecular target, rather than a gene-specific target as would likely be the case, for example of a plasmid-borne gene or product thereof which may be subject to lateral transmission between contemporary organisms.

The discovery that probes could be generated with the extraordinary inclusivity and exclusivity characteristics of those of the present invention with respect to the detection of the etiological agent of Lyme disease, *Borrelia burgdorferi* and its close relatives was unpredictable and unexpected.

BRIEF DESCRIPTION OF THE TABLE AND FIGURE

Further understanding of the principles and aspects of the present invention may be made by reference to the table wherein:

Table 1: Exemplifies the inclusivity and exclusivity behavior of the preferred probes toward a representative sampling of *Borrelia burgdorferi* strains from the United States and Europe, including both clinical and tick isolates, in a dot blot hybridization assay; and by reference to the figure shoving schematic representation of a dual probe capture/detector assay.

FIG. 1: A schematic representation of a sandwich hybridization assay.

DETAILED DESCRIPTION OF THE INVENTION AND BEST MODE

Probe Development Strategy

Figure 1:
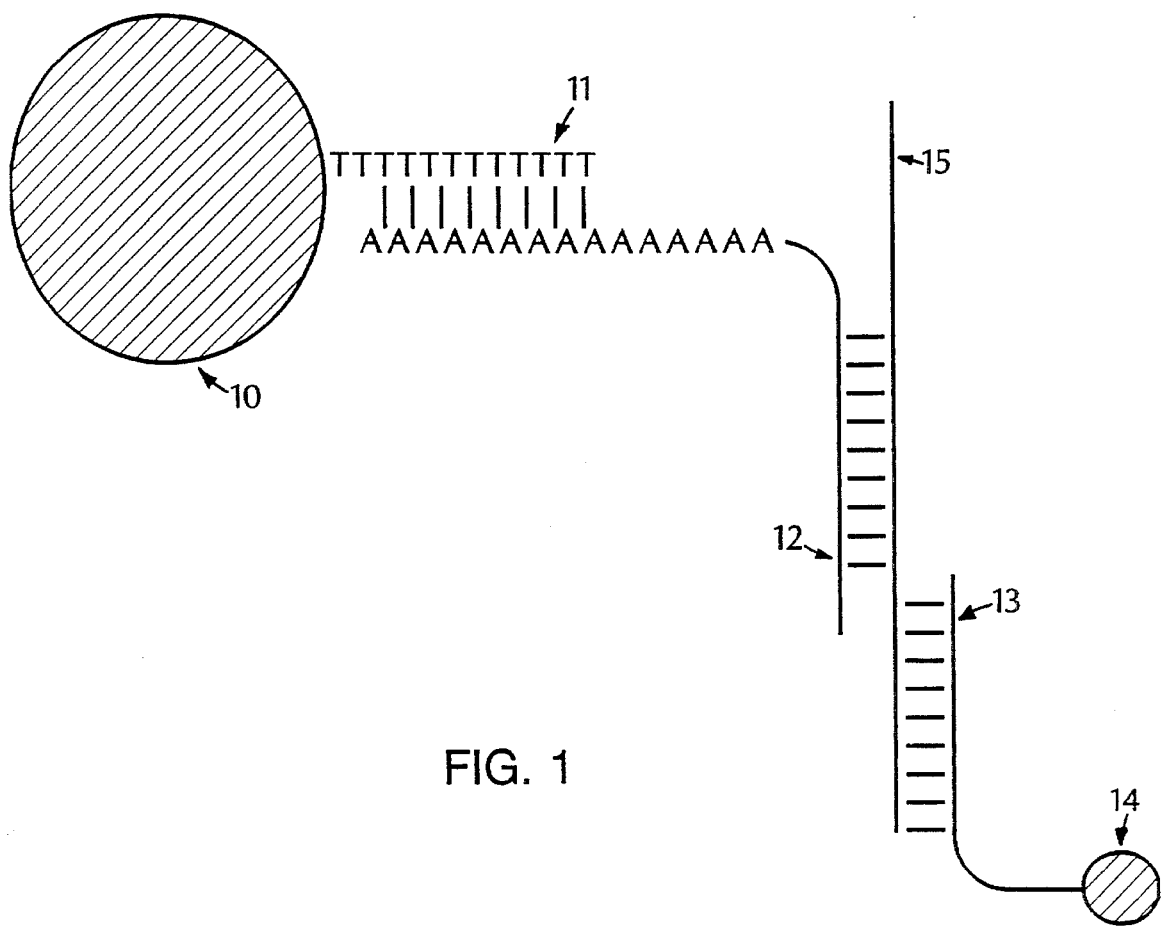

The first step taken in the development of the probes of the present invention involved identification of regions of 16S rRNA which potentially could serve as target sites for Lyme spirochete specific nucleic acid probes. As a practical matter, it is difficult to predict, a priori, which non-Borrelia organisms might be present in any test sample. Of particular import is that probe combinations do not inadvertently detect as Lyme-positive samples actually containing the syphilis spirochete, *Treponema pallidum*.

Because of the large number of such potential non-Lyme agent bacteria, demonstrating exclusivity for any given probe sequence is not only unpredictable but also extremely difficult and laborious. A more rigorous criterion was adopted to obviate the need to know what non-Borrelia bacteria might be present in all test samples that ultimately will be screened using the probes.

This entailed knowledge of the phylogenetic relationships among spirochetes and between spirochetes and other groups of bacteria.

Specifically, an operating but previously unproven hypothesis was adopted that the exclusivity criterion could be satisfied by determining that if a particular target region in *Borrelia burgdorferi* rRNA could be identified which yes sufficiently different from the homologous region in the rRNA of representative yet close evolutionary relatives of *Borrelia burgdorferi*, then a probe to such a sequence could be used to distinguish between *Borrelia burgdorferi* and the relatives by hybridization assay. Based on phylogenetic observations, it then yes extrapolated that rRNA sequences of more distantly related organisms, even though their actual identity may not necessarily be known, should be predictably different in a particular region of sequence than the aforementioned close evolutionary relative of *Borrelia burgdorferi*. However, it cannot be predicted, a priori, whether such regions exist or if they do, where within the rRNA such regions will be located.

Determination of the 16S rRNA sequence from the type strain of *Borrelia burgdorferi*, by standard laboratory methods, and subsequent comparison to sequences of other spirochete 16S rRNAs and to sequences from other blood infectious organisms narrows considerably the search for worthwhile target sequences within the 16S rRNA. Additional evaluation of 16S rRNA sequences from tick-borne bacterial genera, such as Rickettsia and Ehrlichia, capable of causing significant human morbidity or mortality, also contributed to ultimate probe design.

Physical Description of the Probes

The probe selection strategy yielded a number of probes useful for identifying Lyme spirochetes in samples. The following preferred oligonucleotide probes are disclosed herein:

PROBE 1616: 5'-GCCACTGAATGTATTGCTACATCCCGTTG-3' (SEQ ID NO: 1)

PROBE 1617: 5'-CATCAATTAACAAATTAACTGACCTTATT-3' (SEQ ID NO: 2)

PROBE 1618: 5'-CCTCATTTATAAAAGAATTTTACAATCTTTCGACC-3' (SEQ ID NO: 3)

PROBE 1619: 5'-CATCACTTTGTCATTTCCTACAAAGCTTA-3' (SEQ ID NO: 4)

PROBE 1620: 5'-GTTAGCTTCGGTACTAACTTTTAGTTAACACC-3' (SEQ ID NO: 5)

PROBE 1621: 5'-CTTATCTGAGTCCCCACCATTACATGCTGGTAACAG-3' (SEQ ID NO: 6)

PROBE 1622: 5'-CATACCTTAAATACCTTCCTCCCTTACGGGTTAGAATAATA GCTTCGGGTATCCTCAACTCGGG-3' (SEQ ID NO: 7)

These probes target regions within the 16S rRNA with the following analogous target position numbers of *Escherichia coli* 16S rRNA (Brosius et al., PNAS (USA) 75:4801–4805, 1978) and designated target sequences:

PROBE 1616 TARGETS REGION 63–106: 5'-CAAACGGGAUGUAGCAAUACAUUCAGUGGC-3' (SEQ ID NO: 8)

PROBE 1617 TARGETS REGION 178–194: 5'-AAUAAGGUCAGUUAAUUUGUUAAUUGAUG-3' (SEQ ID NO: 9)

PROBE 1618 TARGETS REGION 416–450: 5'-GGUCGAAAGAUUGUAAAAUUCUUUUAUAAA UGAGG-3' (SEQ ID NO: 10)

PROBE 1619 TARGETS REGION 453–481: 5'-UAAGCUUUGUAGGAAAUGACAAAGUGAUG-3' (SEQ ID NO: 11)

PROBE 1620 TARGETS REGION 829–866: 5'-GGUGUUAACUAAAAGUUAGUACCGAAGCU AAC-3' (SEQ ID NO: 12)

PROBE 1621 TARGETS REGION 1122–1156: 5'-CUGUUACCAGCAUGUAAUGGUGGG GACUCAGAUAAG-3' (SEQ ID NO: 13)

PROBE 1622 TARGETS REGION 1414–1475: 5'-CCCGAGUUGAGGAUACCCGAAGCUAUUAUUCUAACCCGUAAGGGAGGAAGGUAUUUAAGGUAUG-3' (SEQ ID NO: 14)

The identification of probe target regions is one of the key aspects of this invention, and enabled the identification of the preferred probes. Each of the probe target regions contains a fundamental core of key nucleotides crucial for creating mismatches with potentially cross-reactive, non-Borrelia organisms. The redesign of the probes by way of shortening the ends, or shifting the probe slightly to one side of the probe target would not be considered a novel redesign of the probe and is contemplated as an equivalent of the probes designated herein.

Two additional oligonucleotides discussed in this invention include:

PROBE/PRIMER 1643: 5'-CCGAATTCGTCGACAACAGAGTTTGATCCTGGCTTAG-3' (SEQ ID NO: 15)

PROBE/PRIMER 1637: 5'-CCCGGGATCCAAGCTTAAGGAGGTGATCCAGCC-3' (SEQ ID NO: 16)

Probe/Primer 1643 is designed to hybridize to the 16S rDNA gene strand complementary to the Borrelia 16S rRNA at its 5' end consisting of the following sequence:

PROBE/PRIMER 1643 TARGET: 5'-CTAAGCCAGGATCAAACTCT-3' (SEQ ID NO: 17)

Probe/Primer 1637 is designed to hybridize to the opposite DNA strand of the preceding target at the 16S rRNA 3' end:

PROBE/PRIMER 1637 TARGET: 5'-GGCTGGATCACCTCCTT-3' (SEQ ID NO: 18)

Oligonucleotides 1643 and 1637 are designed for use in assays employing amplification, by the polymerase chain reaction method, of almost the entire 16S rRNA gene (rDNA) of *Borrelia burgdorferi* and relatives. They are more fully discussed in commonly assigned copending U.S. Ser. No. 359,158 entitled Universal Eubacteria Nucleic Acid Probes and Methods, by Lane et al. and are used in Example 8 regarding Borrelia-specific amplification and detection.

EXAMPLES

EXAMPLE 1

Dot-Blot Analysis of Probe Hybridization Behavior

Dot-blot analysis, in accordance with well known procedures, involves immobilizing a nucleic acid or a population of nucleic acids on a filter such as nitrocellulose, nylon, or other derivatized membranes which can readily be obtained commercially, specifically for this purpose. Either DNA or RNA can be easily immobilized on such a filter and subsequently can be probed or tested for hybridization under any of a variety of conditions (i.e., stringencies) with nucleotide sequences or probes of interest. Under stringent conditions, probes whose nucleotide sequences have greater complementarity to the target will exhibit a higher level of hybridization than probes containing less complementarity.

Probes 1616, 1617, 1618, 1619, 1620, 1621, and 1622 were tested in a dot-blot format. One hundred nanograms of RNA, purified by phenol extraction and centrifugation through cesium triflouracetate gradients, was denatured and spotted on a nylon membrane. Probes were isotopically labelled with the addition of a 32-Phosphorous moiety to the 5' end of the oligonucleotide. Hybridization of probes occurred, at temperatures indicated in Table 1, in the presence of 1.08M sodium chloride, 60 mM sodium phosphate, and 6 mM ethylenediamine tetraacetic acid, pH 7.4. Unhybridized probe was removed by washing at a salt concentration one-third of the hybridization condition. The filters were exposed to X-ray film and the intensity of hybridization signals yes evaluated after three hours of exposure. In the table, "+" represents strong hybridization, "±" represents a faint signal, and "–" designates no signal from hybridization. The dot blot results shown in Table 1 indicate heterogeneity among the *Borrelia burgdorferi* strains and a close relationship to the other Borrelia species.

EXAMPLE 2

Dual Probe Hybridization

In actual practice, many applications of these probes would employ a pair of probes being used simultaneously in a "sandwich" hybridization scheme of "capture" probe and "detector" probe as shown in the Figure. The capture probe[12] ideally would be a bifunctional polynucleotide manufactured by adding a homopolymeric 3' poly-A tail to a probe with high target specificity. The tail would, in turn, hybridize to the complementary homopolymer[11] on a solid surface[10], such as a glass bead, a filter disc, or a magnetic particle. Hybridization of the capture probe[12] to its target[15], in this case Lyme spirochete 16S rRNA, would complex the target[15] with the solid support[10]. The detector probe[13], advantageously also with some degree of specificity, would be part of a preferred detection scheme relying on radioactivity, fluorescence, chemiluminescence, color, etc. (detection moiety[14]) which would report the presence of the entire hybridization complex.

For specific detection of the U.S. Lyme etiological agent, *Borrelia burgdorferi*, for example, a combination of probe 1617 for capture and, 1616, 1618, 1619, 1620, 1621, or 1622 for detection would be the most preferred pair of probes in the preferred assay system. Probe 1620, as a capture probe, for example, would be more completely inclusive for all of the *Borrelia burgdorferi*, but under certain hybridization conditions is inclusive for two other American tick-borne zoonotic pathogens, *Borrelia hermsii* and *Borrelia turicatae*, as well.

EXAMPLE 3

Clinical diagnosis of Lyme disease from human blood sample

Blood is preferably processed so as to yield total nucleic acid content, such as by sonication, vortexing with glass beads, detergent lysis using an agent such as SDS or chemical treatment, or alternatively, bacterial cells are partially purified by, for example, the DuPont Isolator System, followed by cell lysis. Probe 1620, with a polymeric stretch of Adenosine residues attached, and Probe 1621 including a 32-Phosphorous tag, are then ideally combined with the sample in a chaotropic buffer such as guanidinium isothiocyanate. Magnetic particle beads which have been derivatized with oligo-Thymidine also are advantageously included. A hybridization complex comprising the magnetic bead, Probe 1620, target 16S rRNA of *Borrelia burgdorferi* or one of its close relatives and Probe 1621 forms. The exterior presence of a magnet near the bottom of the reaction tube will cause the magnetic particle-hybridization complex to adhere to the interior side of the tube thereby enabling removal of the unreacted components such as the sample matrix, unbound probe, etc. Repeated rehydration and denaturation of the bead-probe-target complex is advantageously performed to enable significant background reduction (as more fully described in U.S. Ser. No. Collins 922,155 EPA 8730938.2). In this example, final detection could entail spotting the beads on membrane and assaying by autoradiography.

EXAMPLE 4

Clinical diagnosis of Lyme disease from other samples.

The procedures set forth in Example Three are ideally followed except, however, that in substitution for the blood sample, one may use a urine sample, skin sample, human synovial fluid, biopsy, or other tissue or fluid. Obvious minor modifications may have to be made in order to accomodate and process the alternative samples to thereby adequately present the target nucleic acid suitably.

EXAMPLE 5

Veterinary diagnosis of Lyme disease

The procedures set forth in Example Three is ideally followed except, however, the sample to be tested is a sample from dog, cat, horse, or other animal. Such a sample may be of the type described in Examples 3 or 4.

EXAMPLE 6

Clinical diagnosis of Lyme disease from human sample employing polymerase chain reaction amplification of Borrelia rDNA Sample processing is designed so as to yield DNA such as the procedures described in Example 3. Probe/Primer 1643 and Probe/Primer 1637 are employed in conjunction with the clinical sample in a polymerase chain reaction. The resultant material can then advantageously be assayed in a "sandwich" hybridization (Example 2) with any of the probes set forth herein. The polymerase chain reaction can, itself, ideally be made highly specific by employing Probe 1643 in conjunction with, for example, Probe 1620 (see FIG. 1). Detection could subsequently be accomplished using any of the Probes: 1616, 1617, 1618, or 1619, or could be measured by incorporation of nucleotide triphosphates into polynucleotides of approximately 850 base pairs in length.

EXAMPLE 7

Test of individual ticks for Borrelia spirochete infection

In order to ascertain the infective potential of ticks within a given area known to be endemic, ticks immobilized by etherization or by freezing are squashed onto nitrocellulose or nylon membrane. Many ticks thusly prepared may be processed simultaneously on the same filter; each individual tick should be approximately 1 cm from any other sample. Filters should then be denatured in base and neutralized as recommended by the manufacturer. Probe 1622, or alternatively, one of the other probes disclosed herein, labelled to high specific activity with 32-Phosphorous is hybridized to the tick panel. After removal of unhybridized probe by washing, the filter is exposed to X-ray film for from 1 to 10 days. Dark spots on the film indicate ticks which contain Lyme spirochetes.

EXAMPLE 8

Test of individual ticks for Borrelia spirochete infection by liquid hybridization A liquid hybridization assay has the advantage of higher sensitivity and ability to perform more than one assay on the same sample, and is therefor preferred over the procedures of Example 7. In this example, individual ticks, such as those removed from human skin are homogenized in chaotropic buffer, and a fraction of this homogenate is assayed in a format analogous to the "sandwich" method described in Example 2.

EXAMPLE 9

Test of ticks from a locality for endemic presence of Lyme disease in an area

A number of ticks from an individual collection site are pooled and homogenized in chaotropic buffer, and assayed as provided in Examples 7 or 8. Positive signal indicates presence of the spirochete in the area, but makes no quantitative evaluation of prevalence.

EXAMPLE 10

In situ hybridization of probe to skin biopsy sample

Skin is one of the better sites to visualize spirochetes, particularly during stage one Lyme disease. A probe, such as for example Probe 1622, is labelled with rhodamine or fluorescein. Skin biopsy, on a slide, is incubated with the fluorescent probe under conditions which foster hybridization and then washed free of unbound probe. Observed under fluorescence microscopy, flourescence of characteristically spiral bacterial cells would be visible.

It will be readily appreciated by those skilled in the art that various modifications to the procedures or probes set forth herein may be made without departing from either the spirit or scope of the present invention. In particular, when modifications of the probes such as by deleting one or two end nucleotides with accompanying adjustments in hybridization conditions are to be deemed equivalent.

TABLE

Lyme Probe Testing - Hybridization to rRNA or cloned rDNA
(HYBRIDIZATION: "+" = strong; "+−" = weak [any above background]; "−" = none)

| | | PROBES Probe Number: | | | | | | | |
|---|---|---|---|---|---|---|---|---|---|
| | | 1616 | | 1617 | | 1618 | | 1619 | |
| | | Approx. 16S location: | | | | | | | |
| | | ~80 | | ~190 | | ~420 | | ~460 | |
| | | Oligomer Size: | | | | | | | |
| | | 29mer | | 29mer | | 35mer | | 29mer | |
| | | Hybridization Temperature: | | | | | | | |
| ATCC or STRAIN | SPECIES NAME (RNAs) | 60 | 50 | 60 | 50 | 60 | 50 | 60 | 50 |
| IG3157 | Escherichia coli | − | − | − | − | − | − | − | − |
| 3391 | Haesophilus influenzas | − | − | − | − | − | − | − | − |
| 13077 | Neisseria meningitidis A | − | − | − | − | − | − | − | − |
| 23448 | Brucella abortus | − | − | − | − | − | − | − | − |
| 6223 | Francisella tularensis | − | − | − | − | − | − | − | − |
| 23059 | Bacillus subtilis | − | − | − | − | − | − | − | − |
| 13124 | Clostridium perfringens | − | − | − | − | − | − | − | − |
| 27340 | Peptostreptococcus productus | − | − | − | − | − | − | − | − |
| 12600 | Staphylococcus aureus | − | − | − | − | − | − | − | − |
| 27534 | Bifidobacterium dentium | − | − | − | − | − | − | − | − |
| 35210 (type-NY) | Borrelia burgdorferi (B31) | + | + | +− | + | +− | + | + | + |
| P/Cu (GERMAN) | Barrelia burgdorfori | +− | + | − | + | +− | + | +− | + |
| MMTI59 (MU) | Borrelia burgdorferi | + | + | +− | + | +− | + | + | + |
| K-48 (CZECH) | Borrelia burgdorferi | + | + | +− | +− | +− | + | + | + |
| I. pacificus | Borrelia burgdorferi | + | + | +− | + | +− | + | + | + |
| MM1 (MNmouse) | Barrelia burgdorferi | + | + | +− | +− | +− | + | + | + |
| veerybird (CONN) | Borrelia burgdorferi | + | + | +− | + | +− | + | + | + |
| PI2699 (CONN) | Borrelia burqdorferi | + | + | +− | + | +− | + | + | + |
| TW GM (TXhuman) | Borrelia burgdorferi | + | + | +− | + | +− | + | + | + |
| CRTdogontick, MN | Borrelia burgdorferi | + | + | +− | + | +− | + | + | + |
| Sparo#5,9789,CT | Borrelia burgdorferi | + | + | +− | + | +− | + | + | + |
| Charlietick (WI) | Borrelia burgdorferi | + | + | +− | + | +− | + | + | + |

TABLE-continued

Lyme Probe Testing - Hybridization to rRNA or cloned rDNA
(HYBRIDIZATION: "+" = strong; "+−" = weak [any above background]; "−" = none)

| | | | | | | | | |
|---|---|---|---|---|---|---|---|---|
| M1J, ECM (LINY) | *Borrelia burgdorferi* | + | + | +− | + | +− | + | + | + |
| 20047P2, Fr.tick | *Borrelia burgdorferi* | + | + | +− | +− | + | + | + | + |
| IP-2 (Fr.CSF) | *Borrelia burgdorferi* | + | + | +− | + | +− | + | + | + |
| N40 (tick NY) | *Borrelia burgdorferi* | + | + | +− | +− | +− | + | + | + |
| M1001 | *Borrelia hermsii* | + | + | +− | +− | +− | + | + | + |
| | *Borrelia turicatae* | + | + | +− | +− | +− | + | + | + |
| 3005 | *Leptonena bifleza illini* | − | − | − | − | − | − | − | − |
| 23581 | *Leptospira interrogans pomona* | − | − | − | − | − | − | − | − |
| 23581 | *Leptospira interrogans* | − | − | − | − | − | − | − | − |
| 23582 | *Leptospira biflexa* (Patoc-Patoc) | − | +− | − | − | − | − | − | − |
| CDC | *Leptospira biflexa* CDC | − | +− | − | − | − | − | − | − |
| | *Spirochaeta aurantia* | − | − | − | − | − | − | − | − |
| rus-1 | *Treponema bryantii* | − | − | − | − | − | − | − | − |
| TD10 | *Treponema denticola* | − | − | − | − | − | − | − | − |
| 33520 | *Treponoma denticola* | − | − | − | − | − | − | − | − |
| 27164 Strain B78 | *Treponema hyodysenteriae* | − | − | − | − | − | − | − | − |
| 27164 Strain 204 | *Traponema hyodysenteriae* | − | − | − | − | − | − | − | − |
| 27164 Strain A-1 | *Treponema hyodysenteriae* | − | − | − | − | − | − | − | − |
| Strain 4/71 | *Treponema innocens* | − | − | − | − | − | − | − | − |
| 33768 | *Treponema pectinovorum* | − | − | − | − | − | − | − | − |
| 6091 | *Treponema succinifaciens* | − | − | − | − | − | − | − | − |
| 25285 | *Bacteroides fragilis* | − | − | − | − | − | − | − | − |
| | Normal Stool RNA | − | − | − | − | − | − | − | − |
| | Wheat Germ RNA | − | − | − | − | − | − | − | − |
| CaSki | Human Cell Line RNA | − | − | − | − | − | − | − | − |
| 18804 | *Candida albicans* | − | − | − | − | − | − | − | − |
| 32045 | *Cryptococcus neoformans* | − | − | − | − | − | − | − | − |
| Lambda Cloned DNAs: | | | | | | | | | |
| cloned rDNA | *Treponema pallidum* | − | − | − | − | − | − | − | − |
| cloned rDNA | *Rickettsia prowazekii* | − | − | − | − | − | − | − | − |
| cloned rDNA | *Ehrlichia risticii* | − | − | − | − | − | − | − | − |

| | | PROBES | | |
|---|---|---|---|---|
| | | Probe Number: | | |
| | | 1621 | 1622 | 1620 |
| | | Approx. 16S location: | | |
| | | ~1140 | ~1450 | ~840 |
| | | Oligomer Size: | | |
| | | 36 mer | 64 mer | 32 mer |
| | | Hybridiation Temperature: | | |
| ATCC or STRAIN | SPECIES NAME (RNAs) | 65 | 50 | 65 | 50 | 65 | 60 | 50 |
|---|---|---|---|---|---|---|---|---|
| IG3157 | *Escherichia coli* | − | − | − | − | − | − | − |
| 3391 | *Haemophilus influenzae* | − | − | − | − | − | − | − |
| 13077 | *Neisseria meningitidis* A | − | − | − | − | − | − | − |
| 23448 | *Brucella abortus* | − | − | − | − | − | − | − |
| 6223 | *Francisella tularensis* | − | − | − | − | − | − | − |
| 23059 | *Bacillus subtilis* | − | − | − | − | − | − | − |
| 13124 | *Clostridium perfringens* | − | − | − | − | − | − | − |
| 27340 | *Peptostreptococcus productus* | − | − | − | − | − | − | − |
| 12600 | *Staphylococcus aureus* | − | − | − | − | − | − | − |
| 27534 | *Bifidobacterium dentium* | − | +− | − | − | − | − | − |
| 35210 (type-NY) | *Borrelia burgdarfori* (B31) | + | + | + | + | + | + | + |
| P/Gu (GERMAN) | *Borrelia burgdorfori* | + | + | + | + | + | + | + |
| MMT159 (MN) | *Borrelia burgdorferi* | + | + | + | + | + | + | + |
| K-48 (CZECH) | *Borrelia burgdorferi* | + | + | + | + | + | + | + |
| *I. pacificus* | *Borrelia burgdorferi* | + | + | + | + | + | + | + |
| MMI (MNmouse) | *Borrelia burgdorferi* | + | + | + | + | + | + | + |
| veerybird (CONN) | *Borrelia burgdorferi* | + | + | + | + | + | + | + |
| PI2699 (CONN) | *Borrelia burgdorferi* | + | + | + | + | + | + | + |
| TH GW (TXhuman) | *Borrelia burqdorferi* | + | + | + | + | + | + | + |
| CRTdogontick, MN | *Borrelia burgdorferi* | + | + | + | + | + | + | + |
| Sparo#5,9789,CT | *Borrelia burgdorferi* | + | + | + | + | + | + | + |
| Charlietick (MI) | *Borrelia burgdorferi* | + | + | + | + | + | + | + |
| M1J, ECH (LINY) | *Borrelia burgdorferi* | + | + | + | + | + | + | + |
| 20047P2, Fr.tick | *Borrelia burgdorferi* | + | + | + | + | + | + | + |
| IP-2 (Fr.CSF) | *Borrelia burgdorferi* | + | + | + | + | + | + | + |

TABLE-continued

Lyme Probe Testing - Hybridization to rRNA or cloned rDNA
(HYBRIDIZATION: "+" = strong; "+−" = weak [any above background]; "−" = none)

| | | | | | | | | |
|---|---|---|---|---|---|---|---|---|
| N40 (tick NY) | *Borrelia burgdorferi* | + | + | + | + | +− | + | + |
| M1001 | *Borrelia hermsii* | +− | + | + | + | − | +− | + |
| | *Borrelia turicatae* | +− | + | + | + | − | +− | + |
| 3005 | *Leptonema biflexa illini* | − | − | − | − | − | − | − |
| 23581 | *Leptospira interrogans pomona* | − | − | − | − | − | − | − |
| 23581 | *Leptospira interrogans* | − | − | − | − | − | − | − |
| 23582 | *Leptaspira biflexa* (Patoc-Patoc) | − | − | − | − | − | − | − |
| CDC | *Leptospira biflexa CDC* | − | − | − | +− | − | − | − |
| | *Spirochaeta aurantia* | − | − | + | + | − | − | − |
| rus-1 | *Treponema bryantii* | − | − | − | +− | − | − | − |
| TD10 | *Treponema denticola* | − | − | + | + | − | − | − |
| 33520 | *Treponema denticola* | − | − | + | + | − | − | − |
| 27164 Strain B78 | *Treponema hyodysenteriae* | − | − | − | − | − | − | − |
| 27164 Strain 204 | *Treponema hyodysenteriae* | − | − | − | − | − | − | − |
| 27164 Strain A-1 | *Troponema hyodynenteriae* | − | − | − | − | − | − | − |
| Strain 4/71 | *Treponema innocens* | − | − | − | − | − | − | − |
| 33768 | *Treponema pectinovorum* | − | − | − | + | − | − | − |
| 6091 | *Treponema succinifaciens* | − | +− | − | +− | − | − | − |
| 25285 | *Bactercides fragilis* | − | − | − | − | − | − | − |
| | Normal Stool RNA | − | − | − | − | − | − | − |
| | Wheat Germ RNA | − | − | − | − | − | − | − |
| CaSki | Human Cell Line RNA | − | − | − | − | − | − | − |
| 18804 | *Candida albicans* | − | − | − | − | − | − | − |
| 32045 | *Cryptococcus neoformans* | − | − | − | − | − | − | − |
| Lambda Cloned DNAs: | | | | | | | | |
| cloned rNA | *Treponema pallidum* | − | − | − | +− | − | − | − |
| cloned rDNA | *Rickettsia prowazekii* | − | − | − | − | − | − | − |
| cloned rDNA | *Ehrlichia risticii* | − | − | − | − | − | − | − |

---

What is claimed is:

1. An isolated nucleic acid probe consisting of a nucleotide sequence identical or fully complementary to a region of the 16S rRNA of *Borrelia burgdorferi* bounded by nucleotide positions 63 to 106, 178 to 194, 416 to 450, 453 to 481, 829 to 866, 1122 to 1156, or 1414 to 1475, which nucleic acid probe preferentially hybridizes to the 16S rRNA or rDNA of Borrelia bacteria over the 16S rRNA or rDNA of non-Borrelia bacteria.

2. An isolated nucleic acid probe of claim 1, wherein said nucleotide sequence is identical or fully complementary to the nucleotide sequence of probe 1616 (SEQ ID NO: 1), 1617 (SEQ ID NO: 2), 1618 (SEQ ID NO: 3), 1619 (SEQ ID NO: 4), 1620 (SEQ ID NO: 5), 1621 (SEQ ID NO: 6), or 1622 (SEQ ID NO: 7).

3. An isolated nucleic acid probe consisting of a nucleotide sequence identical or fully complementary to the nucleotide sequence of probe 1643 (SEQ ID NO: 15) or 1637 (SEQ ID NO: 16).

4. A method for detecting Borrelia bacteria in a biological sample from a patient comprising the steps of:
    a) processing said sample to yield nucleic acid;
    b) contacting said nucleic acid with at least one nucleic acid probe of claim 1;
    c) imposing hybridization conditions on the nucleic acid and said probe to allow said probe to hybridize to rRNA or rDNA of a Borrelia species, if present in said sample, to form nucleic acid complexes, and not to hybridize with rRNA or rDNA of a non-Borrelia organism; and
    d) detecting said nucleic acid complexes as an indication of the presence of a Borrelia species in the sample.

5. The method of claim 4, wherein said nucleic acid probe of said contacting step consists of a nucleotide sequence identical or fully complementary to the nucleotide sequence of probe 1616 (SEQ ID NO: 1), 1617 (SEQ ID NO: 2), 1618 (SEQ ID NO: 3), 1619 (SEQ ID NO: 4), 1620 (SEQ ID NO: 5), 1621 (SEQ ID NO: 6), 1622 (SEQ ID NO: 7), 1643 (SEQ ID NO: 15), or 1637 (SEQ ID NO: 16).

6. The method of claim 4, wherein said contacting step comprises the use of probe 1643 (SEQ ID NO: 15) or probe 1637 (SEQ ID NO: 16) and said detecting step further comprises contacting said sample with a second nucleic acid probe consisting of a nucleotide sequence identical or fully complementary to the nucleotide sequence of probe 1616 (SEQ ID NO: 1), 1617 (SEQ ID NO: 2), 1618 (SEQ ID NO: 3), 1619 (SEQ ID NO: 4), 1620 (SEQ ID NO: 5), 1621 (SEQ ID NO: 6), or 1622 (SEQ ID NO: 7).

7. A new method of claim 4 further comprising the step of amplifying 16S rRNA or rDNA of said Borrelia species, if present, by polymerase chain reaction.

8. A set of nucleic acid probes comprising at least two probes, each probe consisting of a different nucleotide sequence identical or fully complementary to the nucleotide sequence of probe 1616 (SEQ ID NO: 1), 1617 (SEQ ID NO: 2), 1618 (SEQ ID NO: 3), 1619 (SEQ ID NO: 4), 1620 (SEQ ID NO: 5), 1621 (SEQ ID NO: 6), 1622 (SEQ ID NO: 7), 1643 (SEQ ID NO: 15), or 1637 (SEQ ID NO: 16).

9. A set of nucleic acid probes of claim 8, wherein said set consists of any one of probe sets 1616 (SEQ ID NO: 1) and 1617 (SEQ ID NO: 2), 1620 (SEQ ID NO: 5) and 1621 (SEQ ID NO: 6), or 1643 (SEQ ID NO: 15), 1620 (SEQ ID NO: 5), and any one of probes 1616 (SEQ ID NO: 1), 1617 (SEQ ID NO: 2), 1618 (SEQ ID NO: 3), and 1619 (SEQ ID NO: 4).

10. An isolated nucleic acid probe of claim 1, wherein said nucleotide sequence is identical or fully complementary to the nucleotide sequence of probe 1616 (SEQ ID NO: 1).

11. An isolated nucleic acid probe of claim 1, wherein said nucleotide sequence is identical or fully complementary to the nucleotide sequence of probe 1617 (SEQ ID NO: 2).

12. An isolated nucleic acid probe of claim 1, wherein said nucleotide sequence is identical or fully complementary to the nucleotide sequence of probe 1618 (SEQ ID NO: 3).

13. An isolated nucleic acid probe of claim 1, wherein said nucleotide sequence is identical or fully complementary to the nucleotide sequence of probe 1619 (SEQ ID NO: 4).

14. An isolated nucleic acid probe of claim 1, wherein said nucleotide sequence is identical or fully complementary to the nucleotide sequence of probe 1620 (SEQ ID NO: 5).

15. An isolated nucleic acid probe of claim 1, wherein said nucleotide sequence is identical or fully complementary to the nucleotide sequence of probe 1621 (SEQ ID NO: 6).

16. An isolated nucleic acid probe of claim 1, wherein said nucleotide sequence is identical or fully complementary to the nucleotide sequence of probe 1622 (SEQ ID NO: 7).

* * * * *

SEQUENCE LISTING ( 1 ) GENERAL INFORMATION:

( i i i ) NUMBER OF SEQUENCES: 18

( 2 ) INFORMATION FOR SEQ ID NO: 1:

( i ) SEQUENCE CHARACTERISTICS:
  ( A ) LENGTH: 29
  ( B ) TYPE: nucleic acid
  ( C ) STRANDEDNESS: single
  ( D ) TOPOLOGY: linear ( x i ) SEQUENCE DESCRIPTION: SEQ ID NO: 1:

GCCACTGAAT GTATTGCTAC ATCCGTTG  29

( 2 ) INFORMATION FOR SEQ ID NO: 2:

( i ) SEQUENCE CHARACTERISTICS:
  ( A ) LENGTH: 29
  ( B ) TYPE: nucleic acid
  ( C ) STRANDEDNESS: single
  ( D ) TOPOLOGY: linear ( x i ) SEQUENCE DESCRIPTION: SEQ ID NO: 2:

CATCAATTAA CAAATTAACT GACCTTATT  29

( 2 ) INFORMATION FOR SEQ ID NO: 3:

( i ) SEQUENCE CHARACTERISTICS:
  ( A ) LENGTH: 35
  ( B ) TYPE: nucleic acid
  ( C ) STRANDEDNESS: single
  ( D ) TOPOLOGY: linear ( x i ) SEQUENCE DESCRIPTION: SEQ ID NO: 3:

CCTCATTTAT AAAAGAATTT TACAATCTTT CGACC          35

( 2 ) INFORMATION FOR SEQ ID NO: 4:

( i ) SEQUENCE CHARACTERISTICS:
        ( A ) LENGTH: 29
        ( B ) TYPE: nucleic acid
        ( C ) STRANDEDNESS: single
        ( D ) TOPOLOGY: linear ( x i ) SEQUENCE DESCRIPTION: SEQ ID NO: 4:

CATCACTTTG TCATTTCCTA CAAAGCTTA          29

( 2 ) INFORMATION FOR SEQ ID NO: 5:

( i ) SEQUENCE CHARACTERISTICS:
        ( A ) LENGTH: 32
        ( B ) TYPE: nucleic acid
        ( C ) STRANDEDNESS: single
        ( D ) TOPOLOGY: linear ( x i ) SEQUENCE DESCRIPTION: SEQ ID NO: 5:

GTTAGCTTCG GTACTAACTT TTAGTTAACA CC          32

( 2 ) INFORMATION FOR SEQ ID NO: 6:

( i ) SEQUENCE CHARACTERISTICS:
        ( A ) LENGTH: 36
        ( B ) TYPE: nucleic acid
        ( C ) STRANDEDNESS: single
        ( D ) TOPOLOGY: linear ( x i ) SEQUENCE DESCRIPTION: SEQ ID NO: 6:

CTTATCTGAG TCCCCACCAT TACATGCTGG TAACAG          36

( 2 ) INFORMATION FOR SEQ ID NO: 7:

( i ) SEQUENCE CHARACTERISTICS:
        ( A ) LENGTH: 64
        ( B ) TYPE: nucleic acid
        ( C ) STRANDEDNESS: single
        ( D ) TOPOLOGY: linear ( x i ) SEQUENCE DESCRIPTION: SEQ ID NO: 7:

CATACCTTAA ATACCTTCCT CCCTTACGGG TTAGAATAAT AGCTTCGGGT ATCCTCAACT          60

CGGG          64

( 2 ) INFORMATION FOR SEQ ID NO: 8:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO: 8:

CAAACGGGAU GUAGCAAUAC AUUCAGUGGC          30

( 2 ) INFORMATION FOR SEQ ID NO: 9:

( i ) SEQUENCE CHARACTERISTICS:
        ( A ) LENGTH: 29
        ( B ) TYPE: nucleic acid
        ( C ) STRANDEDNESS: single
        ( D ) TOPOLOGY: linear ( x i ) SEQUENCE DESCRIPTION: SEQ ID NO: 9:

AAUAAGGUCA GUUAAUUUGU UAAUUGAUG　　　　　　　　　　　　　　　　　　　　29

( 2 ) INFORMATION FOR SEQ ID NO: 10:

( i ) SEQUENCE CHARACTERISTICS:
    ( A ) LENGTH: 35
    ( B ) TYPE: nucleic acid
    ( C ) STRANDEDNESS: single
    ( D ) TOPOLOGY: linear ( x i ) SEQUENCE DESCRIPTION: SEQ ID NO: 10:

GGUCGAAAGA UUGUAAAAUU CUUUAUAAA UGAGG　　　　　　　　　　　　　　35

( 2 ) INFORMATION FOR SEQ ID NO: 11:

( i ) SEQUENCE CHARACTERISTICS:
    ( A ) LENGTH: 29
    ( B ) TYPE: nucleic acid
    ( C ) STRANDEDNESS: single
    ( D ) TOPOLOGY: linear ( x i ) SEQUENCE DESCRIPTION: SEQ ID NO: 11:

UAAGCUUUGU AGGAAAUGAC AAAGUGAUG　　　　　　　　　　　　　　　　　　　29

( 2 ) INFORMATION FOR SEQ ID NO: 12:

( i ) SEQUENCE CHARACTERISTICS:
    ( A ) LENGTH: 32
    ( B ) TYPE: nucleic acid
    ( C ) STRANDEDNESS: single
    ( D ) TOPOLOGY: linear ( x i ) SEQUENCE DESCRIPTION: SEQ ID NO: 12:

GGUGUUAACU AAAAGUUAGU ACCGAAGCUA AC　　　　　　　　　　　　　　　　32

( 2 ) INFORMATION FOR SEQ ID NO: 13:

( i ) SEQUENCE CHARACTERISTICS:
    ( A ) LENGTH: 36
    ( B ) TYPE: nucleic acid
    ( C ) STRANDEDNESS: single
    ( D ) TOPOLOGY: linear ( x i ) SEQUENCE DESCRIPTION: SEQ ID NO: 13:

CUGUUACCAG CAUGUAAUGG UGGGACUCA GAUAAG　　　　　　　　　　　　　36

( 2 ) INFORMATION FOR SEQ ID NO: 14:

( i ) SEQUENCE CHARACTERISTICS:
    ( A ) LENGTH: 64
    ( B ) TYPE: nucleic acid
    ( C ) STRANDEDNESS: single
    ( D ) TOPOLOGY: linear ( x i ) SEQUENCE DESCRIPTION: SEQ ID NO: 14:

CCCGAGUUGA GGAUACCCGA AGCUAUUAUU CUAACCCGUA AGGGAGGAAG GUAUUUAAGG　60

UAUG　　　　　　　　　　　　　　　　　　　　　　　　　　　　　　　　　　　64

( 2 ) INFORMATION FOR SEQ ID NO: 15:

( i ) SEQUENCE CHARACTERISTICS:
    ( A ) LENGTH: 37
    ( B ) TYPE: nucleic acid
    ( C ) STRANDEDNESS: single -continued ( D ) TOPOLOGY: linear ( x i ) SEQUENCE DESCRIPTION: SEQ ID NO: 15:

CCGAATTCGT CGACAACAGA GTTTGATCCT GGCTTAG   37

( 2 ) INFORMATION FOR SEQ ID NO: 16:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( x i ) SEQUENCE DESCRIPTION: SEQ ID NO: 16:

CCCGGGATCC AAGCTTAAGG AGGTGATCCA GCC   33

( 2 ) INFORMATION FOR SEQ ID NO: 17:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 17:

CTAAGCCAGG ATCAAACTCT   20

( 2 ) INFORMATION FOR SEQ ID NO: 18:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear ( x i ) SEQUENCE DESCRIPTION: SEQ ID NO: 18:

GGCTGGATCA CCTCCTT   17